United States Patent
Ellig et al.

(10) Patent No.: US 10,065,903 B2
(45) Date of Patent: Sep. 4, 2018

(54) PROCESSES FOR PRODUCING HYDROCARBONS FROM A RENEWABLE FEEDSTOCK

(71) Applicant: UOP LLC, Des Plaines, IL (US)

(72) Inventors: Daniel L. Ellig, Arlington Heights, IL (US); Geoffrey W. Fichtl, Chicago, IL (US); Charles P. Luebke, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/220,332

(22) Filed: Jul. 26, 2016

(65) Prior Publication Data

US 2017/0029347 A1 Feb. 2, 2017

Related U.S. Application Data

(60) Provisional application No. 62/199,709, filed on Jul. 31, 2015.

(51) Int. Cl.
*C07C 2/66* (2006.01)
*C11C 3/08* (2006.01)
(Continued)

(52) U.S. Cl.
CPC .............. *C07C 2/66* (2013.01); *C07C 1/2078* (2013.01); *C07C 5/333* (2013.01); *C10G 3/42* (2013.01);
(Continued)

(58) Field of Classification Search
CPC .............. C07C 2/66; C07C 5/333; C10G 3/42
(Continued)

(56) References Cited

U.S. PATENT DOCUMENTS

| 4,784,807 A | 11/1988 | Zinnen |
| 5,770,782 A * | 6/1998 | Knifton .................. B01D 3/322 585/463 |

(Continued)

FOREIGN PATENT DOCUMENTS

| WO | 2008093990 | 8/2008 |
| WO | 2014111598 | 7/2014 |

OTHER PUBLICATIONS

Bezard, J.; Bugaut, M.; Clement, G. "Triglyceride Composition of Coconut Oil", (Mar. 1971), pp. 134-139.*

(Continued)

*Primary Examiner* — Philip Y Louie
*Assistant Examiner* — Aaron W Pierpont

(57) ABSTRACT

Processes for the production of linear alkylbenzenes from a renewable feedstock. Prior to converting the side chains of the glycerides and free fatty acids of the feedstock into hydrocarbons, the feedstock is separated into a stream rich in $C_{10}$ and $C_{14}$ free fatty acids glycerides having $C_{10}$ and $C_{14}$ fatty acid side chains and at least one, preferably two, other glyceride streams. The stream rich in glycerides having $C_{10}$ and $C_{14}$ fatty acid side chains can be converted via deoxygenation into a stream rich in $C_9$ to $C_{14}$ hydrocarbons while the other glyceride streams can be used as vegetable oil. A $C_{10}$ to $C_{13}$ hydrocarbon fraction from the stream rich in $C_9$ to $C_{14}$ hydrocarbons may be dehydrogenated to form olefins which may be reacted with benzene to form linear alkylbenzenes. The linear alkylbenzenes may be used to produce surfactants.

16 Claims, 1 Drawing Sheet

(51) Int. Cl.
*C07C 1/207* (2006.01)
*C07C 5/333* (2006.01)
*C10G 29/20* (2006.01)
*C10G 57/00* (2006.01)
*C10G 3/00* (2006.01)
*C10G 9/00* (2006.01)

(52) U.S. Cl.
CPC .............. *C10G 9/00* (2013.01); *C10G 29/205* (2013.01); *C10G 57/005* (2013.01); *C11C 3/08* (2013.01)

(58) Field of Classification Search
USPC ........................................................ 585/323
See application file for complete search history.

(56) References Cited

U.S. PATENT DOCUMENTS

| 8,502,005 | B1 | 8/2013 | Bozzano et al. |
| 8,766,025 | B2 | 7/2014 | Luebke et al. |
| 8,889,933 | B2 | 11/2014 | Vermeiren et al. |
| 2004/0122246 | A1* | 6/2004 | Sparso ..................... A23D 9/00 554/175 |
| 2007/0131579 | A1* | 6/2007 | Koivusalmi ......... C10M 107/10 208/19 |
| 2013/0317268 | A1* | 11/2013 | Bozzano .................. C01B 3/00 585/251 |
| 2013/0338410 | A1 | 12/2013 | Wang et al. |
| 2014/0024869 | A1* | 1/2014 | Roberts ................. C07C 1/2076 585/310 |

OTHER PUBLICATIONS

Dale, A.P.; Meara, M.L. "The Component Fatty Acids and Glycerides of Coconut Oils", J. Sci. Food. Agric., 6 (1955), pp. 162-166.*

Huang, C.B.; Alimova, Y.; Myers, T.M.; Ebersole, J.L. "Short- and medium-chain fatty acids exhibit antimicrobial activity for oral microorganisms", Archives of Oral Biology, 56 (2011), pp. 650-654.*

Combs, D. L. "Processing for Industrial Fatty Acids—I" JAOCS, 62 (1985), pp. 327-330.*

* cited by examiner

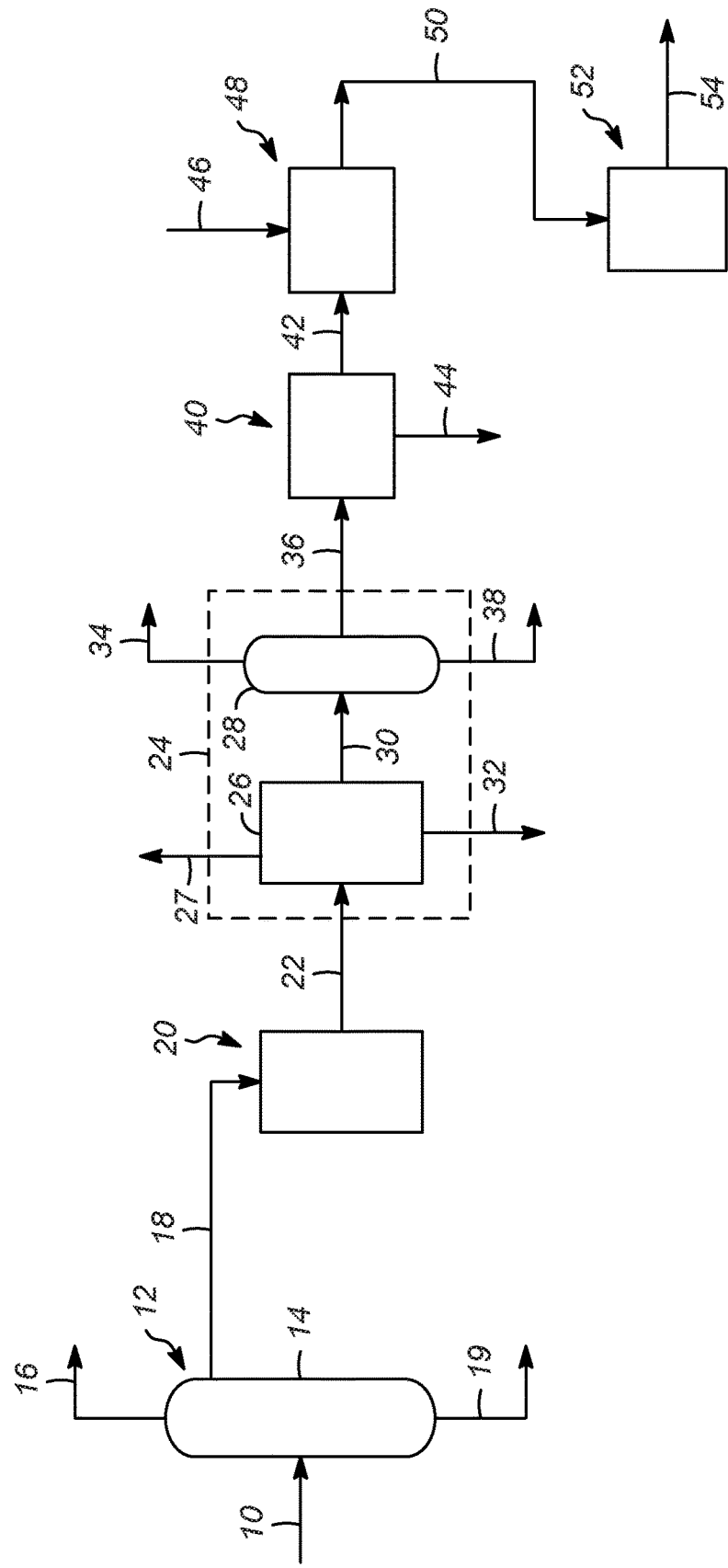

PROCESSES FOR PRODUCING HYDROCARBONS FROM A RENEWABLE FEEDSTOCK

CROSS-REFERENCE TO RELATED APPLICATION

This application claims priority from Provisional Application No. 62/199,709 filed Jul. 31, 2015, the contents of which are hereby incorporated by reference

FIELD OF THE INVENTION

The present invention relates generally to methods for producing hydrocarbons from a renewable feedstock to be used, for example as detergent compounds, and more particularly relates to methods for producing linear alkylbenzenes, paraffins, and olefins from natural oils and kerosene.

BACKGROUND OF THE INVENTION

Linear alkylbenzenes (LABs) are organic compounds with the formula $C_6H_5C_nH_{2n+1}$. While "n" can have any practical value, current commercial use of alkylbenzenes requires that n lie in the range of 10 to 16, or in the range of 8 to 15, or in the range of 10 to 13, or in the range of 12 to 15, or in the range of 9 to 14. These specific ranges are often required when the alkylbenzenes are used as intermediates in the production of surfactants for detergents. Since the surfactants created from alkylbenzenes are biodegradable, the production of alkylbenzenes has grown rapidly since their initial uses in detergent production in the 1960s. The linearity of the paraffin chain in the alkylbenzenes is key to the material's biodegradability and effectiveness as a detergent. A major factor in the final linearity of the alkylbenzenes is the linearity of the paraffin component.

While detergents made utilizing alkylbenzene-based surfactants are biodegradable, many processes for creating alkylbenzenes are not entirely based on renewable sources. Specifically, alkylbenzenes are currently produced from kerosene derived from petroleum that was extracted from the earth. U.S. Pat. Nos. 3,950,448 and 5,276,231 both disclose processes from the production of linear alkylbenzenes from fossil fuel feedstocks. In these processes, linear hydrocarbons and benzene may be combined to form the linear alkylbenzenes. The linear hydrocarbons and benzene may be derived from the processing of petroleum crude oil. However, there is increasing interest in producing chemicals, such as linear alkylbenzenes, from feedstocks other than from petroleum crude oil, at least in part due to the cost uncertainty and limited supply of the petroleum crude oil.

Accordingly, various advances have resulted in processes which produce a linear hydrocarbons from renewable feedstocks having glycerides and fatty acids. The linear hydrocarbon produced by such process can be used in a variety of applications including the production of linear alkylbenzenes. For the production of linear alkylbenzenes, typically only $C_{10}$ to $C_{13}$ normal paraffins are desired. Other normal paraffins produced outside of the $C_{14}$ to $C_{18}$ range are generally desirable for diesel fuel or diesel fuel blending component. Since these hydrocarbons, both larger and smaller, are not desired for linear alkylbenzenes, the processing and treatment of the larger hydrocarbons consumes resources and increases expenses and, therefore, may be not be desired.

Therefore, it would be desirable to have one or more processes for providing a linear hydrocarbons in a desired range suitable for use to produce linear alkylbenzenes while reducing the production and processing of undesirable hydrocarbons.

SUMMARY OF THE INVENTION

One or more processes have been invented for the production of a linear alkylbenzene, paraffin, or olefin product from a natural oil in which only a desired range of fatty acids are converted into hydrocarbons.

Therefore, in a first aspect of the invention, the present invention may be characterized broadly as providing a process for producing a linear hydrocarbon for use in producing a linear alkylbenzene surfactant by: separating a renewable glyceride feedstock in a fractionation zone into a triglyceride stream rich in $C_{10}$ to $C_{14}$ fatty acid side chains and at least one other glyceride steam; deoxygenating the triglyceride stream rich in $C_{10}$ to $C_{14}$ fatty acid side chains in a deoxygenation zone having a catalyst and being operated under deoxygenation conditions to provide a paraffin hydrocarbon stream; dehydrogenating the paraffin hydrocarbon stream in a dehydrogenation zone to provide an olefin hydrocarbon stream; and, alkylating the olefin hydrocarbon stream with an aromatic hydrocarbon stream in an alkylation zone having an alkylation catalyst and being operated under alkylation conditions to provide an alkyl benzene product stream.

In at least one embodiment of the present invention, the fractionation zone comprises at least one fractionation column.

In one or more embodiments of the present invention, the fractionation zone provides the triglyceride stream rich in $C_{10}$ to $C_{14}$ fatty acid side chains, a heavy glyceride steam, and a light glyceride stream. It is contemplated that the process includes recovering at least one of the heavy glyceride stream and the light glyceride stream to be used as vegetable oil. It is further contemplated that the process includes recovering both the heavy glyceride steam and the light glyceride stream to be used as vegetable oil.

In various embodiments of the present invention, the renewable glyceride feedstock comprises an oil rich in triglycerides with $C_{10}$ to $C_{14}$ fatty acids. It is contemplated that the oil rich in triglycerides with $C_{10}$ to $C_{14}$ fatty acids is selected from the group consisting of: coconut oil; palm kernel oil; laurel oil; babassu oil; microbial oils; and mixtures thereof.

In one or more embodiments of the present invention, the process includes sulfonating the alkyl benzene product stream to provide a surfactant product.

In a second aspect of the present invention, the present invention may be broadly characterized as providing a process for producing a linear hydrocarbon for use in producing a linear alkylbenzene surfactant by: passing a renewable glyceride feedstock to a fractionation zone to separate the renewable glyceride feedstock into a triglyceride stream rich in $C_{10}$ to $C_{14}$ fatty acid side chains and at least one other glyceride steam; passing the triglyceride stream rich in $C_{10}$ to $C_{14}$ fatty acid side chains to a deoxygenation zone having a catalyst and being operated under deoxygenation conditions to provide a paraffin hydrocarbon stream; passing the paraffin hydrocarbon stream to a dehydrogenation zone to provide an olefin hydrocarbon stream; and, passing the olefin hydrocarbon stream and an aromatic hydrocarbon stream comprising benzene to an alkylation zone having an alkylation catalyst and being operated under alkylation conditions to provide an alkyl benzene product stream.

In one or more embodiments of the present invention, the process includes: sulfonating the alkyl benzene product stream to provide a surfactant product. It is contemplated that the fractionation zone provides the triglyceride stream rich in $C_{10}$ to $C_{14}$ fatty acid side chains, a heavy glyceride stream, and a light glyceride stream. It is also contemplated that the process includes recovering at least one of the heavy glyceride stream and the light glyceride stream to be used as vegetable oil.

In some embodiments of the present invention, the process includes recovering both the heavy glyceride stream and the light glyceride stream to be used as vegetable oil.

In various embodiments of the present invention, the renewable glyceride feedstock is selected from the group consisting of: coconut oil; palm kernel oil; laurel oil; babassu oil; microbial oils; and, mixtures thereof.

In at least one embodiment of the present invention, the renewable glyceride feedstock comprises an oil rich in glycerides having $C_{10}$ to $C_{14}$ fatty acid side chains.

In one or more embodiments of the present invention, the fractionation zone comprises a fractionation column. It is contemplated that the fractionation column provides a light glyceride stream, the triglyceride stream rich in $C_{10}$ to $C_{14}$ fatty acid side chains, and a heavy glyceride stream.

In a third aspect of the present invention, the present invention may be broadly characterized as providing a process for producing a linear hydrocarbon for use in producing a linear alkylbenzene surfactant by: passing a renewable glyceride feedstock to a separation zone configured to separate the renewable glyceride feedstock into a light glyceride stream, a triglyceride stream rich in $C_{10}$ to $C_{14}$ fatty acid side chains, and a heavy glyceride stream; recovering at least one of the heavy glyceride stream and the light glyceride stream to be used as vegetable oil; passing the triglyceride stream rich in $C_{10}$ to $C_{14}$ fatty acid side chains to a deoxygenation zone having a catalyst and being operated under deoxygenation conditions to provide a paraffin hydrocarbon stream; passing the paraffin hydrocarbon stream to a dehydrogenation zone to provide an olefin hydrocarbon stream; and, passing the olefin hydrocarbon stream and an aromatic hydrocarbon stream comprising benzene to an alkylation zone having an alkylation catalyst and being operated under alkylation conditions to provide an alkyl benzene product stream.

In various embodiments of the present invention, the separation zone comprises a fractionation column.

In some embodiments of the present invention, the separation zone comprises a crystallizer.

Additional aspects, embodiments, and details of the invention which may be combined in any manner are set forth in the following detailed description of the invention.

BRIEF DESCRIPTION OF THE DRAWING

One or more exemplary embodiments of the present invention will be described below in conjunction with the following drawing FIGURE, in which:

The FIGURE shows a processes flow diagram according to one or more embodiments of the present invention.

DETAILED DESCRIPTION OF THE INVENTION

As mentioned above, various processes have been invented to produce $C_{10}$ to $C_{13}$ normal paraffins from renewable feedstocks for use as a component in linear alkylbenzenes. In accordance with various embodiments of the present invention, in order to minimize the quantity of diesel and naphtha produced and maximize the quantity of $C_{10}$ to $C_{13}$ normal paraffins produced, the renewable feedstocks is separated into different fractions by some means of separation before converting one fraction to hydrocarbons. Common separation techniques that could be applied include distillation and crystallization.

With these general principles in mind, one or more embodiments of the present invention will be described with the understanding that the following description is not intended to be limiting.

An exemplary process for producing a linear alkylbenzene, paraffin, and/or olefin product is depicted in the FIGURE in which a renewable feedstock 10 is passed to a separation zone 12. The renewable feedstock 10 comprises natural oils. As used herein, natural oils are those derived from plant or algae matter, and are often referred to as renewable oils. Natural oils are not based on kerosene or other fossil fuels. In certain embodiments, the natural oils include, but are not limited to, one or more of coconut oil, babassu oil, castor oil, algae 1 byproduct, beef tallow oil, borage oil, camelina oil, Canola® oil, choice white grease, coffee oil, corn oil, *Cuphea Viscosissima* oil, evening primrose oil, fish oil, hemp oil, hepar oil, jatropha oil, *Lesquerella Fendleri* oil, linseed oil, *Moringa Oleifera* oil, mustard oil, neem oil, palm oil, perilla seed oil, poultry fat, rice bran oil, soybean oil, stillingia oil, sunflower oil, tung oil, yellow grease, cooking oil, and other vegetable, nut, seed oils or animal fats. Other natural oils will be known to those having ordinary skill in the art. The natural oils typically include triglycerides, free fatty acids, or a combination of both, and other trace compounds. Furthermore, it is also contemplated that the oils are microbial oils, which are oils that produced by microbes or other organisms, including genetically modified or engineered microbes that produce oils, and preferably with desired side chain lengths.

In various embodiments of the present invention, the renewable feedstock 10 preferably comprises an oil having glycerides, preferably triglycerides having at least one $C_{10}$ to $C_{14}$ fatty acid side chain, such as coconut oil, palm kernel oil, laurel oil, babassu oil, and, mixtures thereof. As is known, the oils comprise glycerides having between one and three fatty acids bonded together with a glycerol bridge. As discussed in more detail below, when the glycerides and more particular the fatty acid side chains on the glyceride are converted (e.g., deoxygenated) into hydrocarbons, the fatty acids will typically convert to paraffins that have either the same or one fewer carbon atoms than the fatty acid side chain from which they are derived. Therefore, an oil rich in $C_{10}$ to $C_{14}$ free fatty acids and glycerides rich in $C_{10}$ to $C_{14}$ fatty acid side chains, will produce an effluent having a high amount of $C_{10}$ to $C_{14}$ hydrocarbons via the conversion. By "$C_{10}$ to $C_{14}$ fatty acids," we mean one or more of glycerides having fatty acid side chains having 10 to 14 carbon atoms, glycerides having fatty acid side chains which when deoxygenated form paraffins having 10 to 14 carbon atoms (e.g., coconut oil), and free fatty acids having between 10 and 14 carbon atoms. By "rich in $C_{10}$ to $C_{14}$ fatty acids," we mean that the feedstock contains at least about 50 wt % of fatty acids having between 10 and 14 carbon atoms, or greater than about 55 wt %, or greater than about 60 wt %, or greater than about 65 wt %, or greater than about 65 wt %.

Returning to the FIGURE, the separation zone 12 may include any suitable technology or process for separating the glycerides of the renewable feedstock 10. For example, the separation zone may include a fractionation column 14 or a crystallization unit. The particular equipment used to separate the renewable feedstock 10 is not important to the practicing or understanding of the present invention. The separation zone 12 separates the renewable feedstock 10 into at least two streams 16, 18, and preferably at least three streams 16, 18, 19.

The first stream 16 from the separation zone 12 may comprise a light triglyceride stream that includes, in one embodiment, triglycerides that include $C_8$ and lighter fatty acid side chains. The second stream 18 from the separation zone 12 may comprise a stream rich in $C_{10}$ to $C_{14}$ fatty acid, most preferably rich in glycerides, preferably triglycerides, having one or more $C_{10}$ to $C_{14}$ fatty acid side chains. The third stream 19 from the separation zone 12 comprises glycerides that include one or more $C_{14}$ and heavier fatty acid side chains. It should be appreciated that there may be some overlap between the various streams and that the composition of the streams refers to the dominant component, and does not exclude other components.

The further processing of the first stream 16 and the third stream 19 is not necessary for the understanding and practicing of the present invention. In various embodiments, the first stream 16, the third stream 19, or both are used in normal vegetable oil for other use. Alternatively, the first stream 16, the third stream 19, or both can be processed and converted into linear hydrocarbons for use, for example as a transportation fuel. Furthermore, if the renewable feedstock 10 includes a significant portion of free fatty acids, especially, $C_{10}$ to $C_{14}$ free fatty acids, the separation zone 12 may include equipment such as a column to separate the fatty acids into one or more streams, and equipment such as a column to separate the glycerides into various stream, which may be combined with the streams of free fatty acids.

Returning to the second stream 18 from the separation zone 12, the second stream 18 is passed to a reaction zone 20 to convert the glycerides (and more particularly the fatty acid side chains of the glycerides) into linear hydrocarbons. In a preferred embodiment, the reaction zone 20 comprises a deoxygenation zone in which the fatty acid side chains in the triglycerides and free fatty acids in the second stream 18 are deoxygenated and converted into linear paraffins, using a catalyst that is suitable for deoxygenation.

As mentioned above, triglycerides are formed by three, typically different, fatty acid molecules that are bonded together with a glycerol bridge. The glycerol molecule includes three hydroxyl groups (HO—), and each fatty acid molecule has a carboxyl group (COON)— which shares an oxygen atom with the corresponding hydroxyl group. In triglycerides, the hydroxyl groups of the glycerol join the carboxyl groups of the fatty acids to form ester bonds. Therefore, during deoxygenation, the fatty acids are freed from the triglyceride structure and are converted into linear paraffins. The glycerol is converted into propane, and the oxygen in the hydroxyl and carboxyl groups is converted into either water or carbon dioxide. Deoxygenation can occur via two major pathways, where the oxygen atoms of the triglyceride either combine with available hydrogen to form water ($H_2O$), known as hydrodeoxygenation, or retain their linkage to the first carbon of the fatty chain and convert to carbon dioxide ($CO_2$) or carbon monoxide (CO), known as decarboxylation and decarbonylation, respectively. Hydrodeoxygenation and decarboxylation/decarbonylation occur simultaneously and both result in the fatty acids breaking their links to the three-carbon backbone of the triglyceride, such that water, carbon oxides, and propane are evolved. With CO, $CO_2$, $H_2O$, and $H_2$ simultaneously present, the Water-Gas shift reaction will shift $CO_2$ and $H_2$ into CO and $H_2O$, or vice versa, depending on the catalyst selection and reaction conditions. Once deoxygenated and saturated, the fatty acid chains of the original triglyceride have been converted to long linear paraffin chains (normal alkanes) that are fully hydrocarbon.

An exemplary deoxygenation zone is disclosed for example in U.S. Pat. No. 8,039,682, the entirety of which is incorporated herein by reference. In general, the deoxygenation zone includes one or more reactors comprising a suitable catalyst(s) for promoting deoxygenation reactions and which may be any of those well known in the art such as nickel or nickel/molybdenum dispersed on a high surface area support. Other catalysts include one or more noble metal catalytic elements dispersed on a high surface area support. Non-limiting examples of noble metals include Pt and/or Pd dispersed on gamma-alumina. Generally, deoxygenation conditions include a temperature of about 40 to about 700° C. (104 to 1,292° F.) and a pressure of about 700 to about 21 MPa (100 to 3,000 psig). Other operating conditions for the deoxygenation zone 20 are well known in the art.

As shown in the FIGURE, a deoxygenation effluent stream 22 may be passed from the reaction zone 20 to a separation zone 24 to separate the desired linear paraffins from the branched compounds, the cyclic compounds and the undesired linear hydrocarbons that may be included in the deoxygenation effluent stream 22. In one embodiment, the separation zone 24 may comprise a separator 26 and a fractionation column 28. The separator 26 can be either a cold or hot separator and is used to remove the byproducts of the deoxygenation zone 20 reactions. If the separator 26 comprises a cold separator, a water stream 32 may be removed as a liquid from the bottom of the separator 26. If the separator 26 comprises a hot separator is used, water may be removed in a vapor stream 27 from the overhead of the separator 26. In either case, the vapor stream 27 from the separator 26 will comprise at least propane and light ends, carbon oxides and hydrogen sulfide. Additionally, in either mode, the vapor stream 27 from the separator 26 may comprise at least some water vapor.

The carbon oxides and hydrogen sulfide may be removed from the vapor stream 27 by techniques such as scrubbing. Suitable scrubbing techniques are described in U.S. Pat. No. 7,982,077 and U.S. Pat. No. 7,982,078 each hereby incorporated by reference in its entirety. After the carbon oxides and/or the hydrogen sulfide has been removed from the vapor stream 27, the propane and other light ends may be, for example, directed to an optional steam reforming zone (not shown). If the separator 26 is operated as a hot separator and water vapor is present in the separator overhead, the water may be optionally retained in the carbon oxide and hydrogen sulfide scrubber, condensed from the hydrocarbon stream, or co-fed with the light ends to the steam reformer.

The temperature of the separator 26 may be from about ambient temperature to about 454° C. (about 850° F.), and the pressure may be from about 1379 kPa gauge to about 13,790 kPa gauge (200 to about 2,000 psig). In one embodiment, the temperature is from about 150° C. to about 454° C. (about 300° F. to about 850° F.).

The fractionation column 28 in the separation zone 24 separates the linear hydrocarbons 30 into one or more streams, for example, a light ends stream 34, a desired paraffin hydrocarbon stream 36, and a heavy stream 38. In the present application, the desired paraffin hydrocarbon stream 36 comprises mostly $C_{10}$ to $C_{13}$ hydrocarbons, with the understanding that some lighter and some heavier components may also be contained therein. Accordingly, in cases in which the desired hydrocarbon stream 36 comprises mostly $C_{10}$ to $C_{13}$ hydrocarbons, the light hydrocarbon stream 34 may comprises $C_{9-}$ hydrocarbons, while the heavy stream 38 may comprises $C_{14+}$ hydrocarbons.

The desired paraffin hydrocarbon stream 36 may be passed to a dehydrogenation zone 40 to provide an olefin hydrocarbon stream 42. Although not depicted as such, one or more of the streams from the fractionation column 28 may be directed first to a purification zone (not shown) to remove any remaining trace contaminants, such as oxygenates, nitrogen compounds, and sulfur compounds, among others, that were not previously removed in the processing steps described above.

In the dehydrogenation zone 40, the desired paraffin hydrocarbon stream 36 is dehydrogenated into olefins, preferably predominantly mono-olefins. Typically, dehydrogenation occurs through known catalytic processes, such as the commercially popular Pacol process. Conversion is typically less than about 30%, for example less than about 20%, leaving greater than about 70% paraffins unconverted to olefins. Di-olefins (i.e., dienes) and aromatics are also produced as an undesired result of the dehydrogenation reactions. In order to convert the di-olefins to mono-olefins, the dehydrogenation zone 40 may include a selective hydrogenation zone such as a DeFine® reactor (or a reactor employing a DeFine® process), available from UOP LLC. The hydrogenation unit is configured to selectively hydrogenate at least a portion of the di-olefins. As a result, the olefin stream 42 form the dehydrogenation zone 40 will have an increased mono-olefin concentration. The dehydrogenation zone 40 may also include a separation zone configured to separate the desired olefins from the unconverted converted paraffins 44, which may be recycled as feed to the dehydrogenation zone 40. An olefin hydrocarbon stream 42 from the dehydrogenation zone 40 and a benzene stream 46 may be passed to an alkylation zone 48.

The alkylation zone 48 comprises one or more reactors having a catalyst, such as a solid acid catalyst, that supports alkylation of the benzene with the mono-olefins. Hydrogen fluoride (HF) and aluminum chloride ($AlCl_3$) are two major catalysts in commercial use for the alkylation of benzene with linear mono-olefins and may be used in the alkylation zone 48. Additional catalysts include zeolite-based or fluoridate silica alumina-based solid bed alkylation catalysts (for example, FAU, MOR, UZM-8, Y, X RE exchanged Y, RE exchanged X, amorphous silica-alumina, and mixtures thereof, and others known in the art). As a result of alkylation, alkylbenzene, typically called linear alkylbenzene is produced. An effluent from the alkylation zone 48 may include unreacted benzene and other compounds which may be separated from an alkylbenzene product stream 50.

The alkylbenzene product stream 50 may be passed to a sulfonation zone 52 in which the linear alkylbenzene will be sulfonated and neutralized with sodium hydroxide to produce a surfactant product stream 54.

In the various processes according to the present invention, yield losses and undesired conversion costs associated with processing undesirable fatty acid side chains and free fatty acids have been minimized due to the separation of the feedstock prior to converting it into hydrocarbons. Thus, the conversion into hydrocarbons will be focused on those molecules most capable of forming hydrocarbons in the desired or target hydrocarbon product range—in the case of linear alkylbenzene $C_{10}$ to $C_{13}$ hydrocarbons. Additionally, further benefits can be obtained by selecting an oil as a feedstock that is rich in fatty acids that may be converted into hydrocarbons within the desired or target hydrocarbon product range.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing a linear hydrocarbon for use in producing a linear alkyl benzene surfactant, the process comprising separating a renewable feedstock in a separation zone into a glyceride stream rich $C_{10}$ to $C_{14}$ fatty acids and at least one other glyceride steam; deoxygenating the glyceride stream rich in glycerides with $C_{10}$ to $C_{14}$ fatty acid side chains in a deoxygenation zone having a catalyst and being operated under deoxygenation conditions to provide a paraffin hydrocarbon stream, dehydrogenating the paraffin hydrocarbon stream in a dehydrogenation zone to provide an olefin hydrocarbon stream, and, alkylating the olefin hydrocarbon stream with an aromatic hydrocarbon stream in an alkylation zone having an alkylation catalyst and being operated under alkylation conditions to provide an alkyl benzene product stream. An embodiment of the invention is one, any or all of prior embodiments in this paragraph up through the first embodiment in this paragraph wherein the separation zone comprises at least one fractionation column. An embodiment of the invention is one, any or all of prior embodiments in this paragraph up through the first embodiment in this paragraph wherein the fractionation zone provides the glyceride stream rich in glycerides with $C_{10}$ to $C_{14}$ fatty acid side chains, a heavy glyceride steam, and a light glyceride stream. An embodiment of the invention is one, any or all of prior embodiments in this paragraph up through the first embodiment in this paragraph further comprising recovering at least one of the heavy glyceride stream and the light glyceride stream to be used as vegetable oil. An embodiment of the invention is one, any or all of prior embodiments in this paragraph up through the first embodiment in this paragraph further comprising recovering both the heavy glyceride steam and the light glyceride stream to be used as vegetable oil. An embodiment of the invention is one, any or all of prior embodiments in this paragraph up through the first embodiment in this paragraph, wherein the renewable glyceride feedstock comprises an oil rich in glycerides with $C_{10}$ to $C_{14}$ fatty acid side chains. An embodiment of the invention is one, any or all of prior embodiments in this paragraph up through the first embodiment in this paragraph, wherein the oil rich in glycerides with $C_{10}$ to $C_{14}$ fatty acid side chains is selected from the group consisting of: coconut oil; palm kernel oil; laurel oil; babassu oil; microbial oils; and, mixtures thereof. An embodiment of the invention is one, any or all of prior embodiments in this paragraph up through the first embodiment in this paragraph further comprising sulfonating the alkyl benzene product stream to provide a surfactant product.

A second embodiment of the invention is a process for producing a linear hydrocarbon for use in producing a linear alkyl benzene surfactant, the process comprising passing a renewable glyceride feedstock to a separation zone to separate the renewable glyceride feedstock into a glyceride stream rich in glycerides with $C_{10}$ to $C_{14}$ fatty acid side chains and at least one other glyceride steam, passing the glyceride stream rich in glycerides with $C_{10}$ to $C_{14}$ fatty acid side chains to a deoxygenation zone having a catalyst and being operated under deoxygenation conditions to provide a paraffin hydrocarbon stream; passing the paraffin hydrocarbon stream to a dehydrogenation zone to provide an olefin hydrocarbon stream, and, passing the olefin hydrocarbon stream and an aromatic hydrocarbon stream comprising benzene to an alkylation zone having an alkylation catalyst and being operated under alkylation conditions to provide an alkyl benzene product stream. An embodiment of the invention is one, any or all of prior embodiments in this paragraph up through the second embodiment in this paragraph further comprising sulfonating the alkyl benzene product stream to provide a surfactant product. An embodiment of the invention is one, any or all of prior embodiments in this paragraph up through the second embodiment in this paragraph wherein the separation zone provides the triglyceride stream rich in $C_{10}$ to $C_{14}$ fatty acids, a heavy glyceride steam, and a light glyceride stream. An embodiment of the invention is one, any or all of prior embodiments in this paragraph up through the second embodiment in this paragraph further comprising recovering at least one of the heavy glyceride stream and the light glyceride stream to be used as vegetable oil. An embodiment of the invention is one, any or all of prior embodiments in this paragraph up through the second embodiment in this paragraph further comprising separating the paraffin hydrocarbon stream into at a $C_{10}$ to $C_{13}$ hydrocarbon stream and at least one other paraffin stream; and, passing the $C_{10}$ to $C_{13}$ hydrocarbon stream to a dehydrogenation zone. An embodiment of the invention is one, any or all of prior embodiments in this paragraph up through the second embodiment in this paragraph, wherein the renewable glyceride feedstock is selected from the group consisting of: coconut oil; palm kernel oil; laurel oil; babassu oil; microbial oils; and mixtures thereof. An embodiment of the invention is one, any or all of prior embodiments in this paragraph up through the second embodiment in this paragraph, wherein the renewable glyceride feedstock comprises an oil rich in glycerides having $C_{10}$ to $C_{14}$ fatty acid side chains. An embodiment of the invention is one, any or all of prior embodiments in this paragraph up through the second embodiment in this paragraph wherein the separation zone comprises a fractionation column. An embodiment of the invention is one, any or all of prior embodiments in this paragraph up through the second embodiment in this paragraph wherein the fractionation column provides a light glyceride stream, the glyceride stream rich in glycerides with $C_{10}$ to $C_{14}$ fatty acid side chains, and a heavy glyceride stream.

A third embodiment of the invention is a process for producing a linear hydrocarbon for use in producing a linear alkyl benzene surfactant, the process comprising passing a renewable glyceride feedstock to a separation zone configured to separate the renewable glyceride feedstock into a light glyceride stream, a glyceride stream rich in glycerides with $C_{10}$ to $C_{14}$ fatty acid side chains, and a heavy glyceride stream, recovering at least one of the heavy glyceride stream and the light glyceride stream to be used as vegetable oil; passing the glyceride stream rich in glycerides with $C_{10}$ to $C_{14}$ fatty acid side chains to a deoxygenation zone having a catalyst and being operated under deoxygenation conditions to provide a paraffin hydrocarbon stream, passing the paraffin hydrocarbon stream to a dehydrogenation zone to provide an olefin hydrocarbon stream, and, passing the olefin hydrocarbon stream and an aromatic hydrocarbon stream comprising benzene to an alkylation zone having an alkylation catalyst and being operated under alkylation conditions to provide an alkyl benzene product stream. An embodiment of the invention is one, any or all of prior embodiments in this paragraph up through the third embodiment in this paragraph wherein the separation zone comprises a crystallizer. An embodiment of the invention is one, any or all of prior embodiments in this paragraph up through the third embodiment in this paragraph further comprising separating the paraffin hydrocarbon stream into at a $C_{10}$ to $C_{13}$ hydrocarbon stream and at least one other paraffin stream; and, passing the $C_{10}$ to $C_{13}$ hydrocarbon stream to a dehydrogenation zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A process for producing a linear mono-olefin hydrocarbon stream for use in producing a linear alkyl benzene product stream, the process comprising:
   distilling a renewable feedstock comprising one or more natural oils derived from plant or algae matter in a separation zone to provide a light glyceride stream that includes $C_8$ and lighter fatty acid side chains, a glyceride stream rich in glycerides with $C_{10}$ to $C_{14}$ fatty acid side chains, and at least one other glyceride stream;
   deoxygenating the glyceride stream rich in glycerides with $C_{10}$ to $C_{14}$ fatty acid side chains in a deoxygenation zone having a catalyst to provide a paraffin hydrocarbon stream;
   dehydrogenating the paraffin hydrocarbon stream in a dehydrogenation zone to provide a linear mono-olefin hydrocarbon stream; and
   alkylating the linear mono-olefin hydrocarbon stream with benzene in an alkylation zone having an alkylation catalyst to provide a linear alkyl benzene product stream.

2. The process of claim 1 wherein the separation zone comprises at least one fractionation column.

3. The process of claim 1 wherein the at least one other glyceride stream comprises a heavy glyceride stream that includes one or more $C_{14}$ and heavier fatty acid side chains.

4. The process of claim 3 further comprising:
recovering at least one of the heavy glyceride stream and the light glyceride stream to be used as vegetable oil.

5. The process of claim 3 further comprising:
recovering both the heavy glyceride stream and the light glyceride stream to be used as vegetable oil.

6. The process of claim 1, wherein the renewable feedstock comprises a natural oil rich in glycerides with $C_{10}$ to $C_{14}$ fatty acid side chains.

7. The process of claim 6, wherein the natural oil rich in glycerides with $C_{10}$ to $C_{14}$ fatty acid side chains is selected from the group consisting of: coconut oil; palm kernel oil; laurel oil; babassu oil; microbial oils; and mixtures thereof.

8. The process of claim 1 further comprising:
sulfonating the linear alkyl benzene product stream to provide a surfactant product.

9. A process for producing a linear mono-olefin hydrocarbon stream for use in producing a linear alkyl benzene product stream, the process comprising:
passing a renewable glyceride feedstock to a separation zone;
distilling the renewable glyceride feedstock to provide a light glyceride stream that includes $C_8$ and lighter fatty acid side chains, a glyceride stream rich in glycerides with $C_{10}$ to $C_{14}$ fatty acid side chains, and at least one other glyceride stream comprising glycerides that include one or more $C_{14}$ and heavier fatty acid side chains;
passing the glyceride stream rich in glycerides with $C_{10}$ to $C_{14}$ fatty acid side chains to a deoxygenation zone having a catalyst to provide a paraffin hydrocarbon stream;
passing at least a portion of the paraffin hydrocarbon stream to a dehydrogenation zone to provide a linear mono-olefin hydrocarbon stream;
passing the linear mono-olefin hydrocarbon stream and benzene to an alkylation zone having an alkylation catalyst to provide a linear alkyl benzene product stream; and
recovering the light glyceride stream and the at least one other glyceride stream to be used as a vegetable oil.

10. The process of claim 9 further comprising:
sulfonating the linear alkyl benzene product stream to provide a surfactant product.

11. The process of claim 10, wherein the paraffin hydrocarbon stream comprises $C_{10}$ to $C_{13}$ hydrocarbons and wherein passing at least a portion of the paraffin hydrocarbon stream to the dehydrogenation zone comprises: separating the paraffin hydrocarbon stream into a $C_{10}$ to $C_{13}$ hydrocarbon stream and at least one other paraffin stream; and
passing the $C_{10}$ to $C_{13}$ hydrocarbon stream to the dehydrogenation zone.

12. The process of claim 10, wherein the renewable glyceride feedstock is selected from the group consisting of: coconut oil; palm kernel oil; laurel oil; babassu oil; microbial oils; and mixtures thereof.

13. The process of claim 10, wherein the renewable glyceride feedstock comprises an oil rich in glycerides having $C_{10}$ to $C_{14}$ fatty acid side chains.

14. The process of claim 9 wherein the separation zone comprises a fractionation column.

15. A process for producing a linear mono-olefin hydrocarbon stream for use in producing a linear alkyl benzene product stream, the process comprising:
passing a renewable glyceride feedstock to a separation zone;
distilling the renewable glyceride feedstock to provide a light glyceride stream that includes $C_8$ and lighter fatty acid side chains, a glyceride stream rich in glycerides with $C_{10}$ to $C_{14}$ fatty acid side chains, and a heavy glyceride stream;
recovering at least one of the heavy glyceride stream and the light glyceride stream to be used as vegetable oil;
passing the glyceride stream rich in glycerides with $C_{10}$ to $C_{14}$ fatty acid side chains to a deoxygenation zone having a catalyst to provide a paraffin hydrocarbon stream;
passing at least a portion of the paraffin hydrocarbon stream to a dehydrogenation zone to provide a linear mono-olefin hydrocarbon stream; and
passing the linear mono-olefin hydrocarbon stream and benzene to an alkylation zone having an alkylation catalyst to provide a linear alkyl benzene product stream.

16. The process of claim 15, wherein the paraffin hydrocarbon stream comprises $C_{10}$ to $C_{13}$ hydrocarbons and wherein passing at least a portion of the paraffin hydrocarbon stream to the dehydrogenation zone comprises: separating the paraffin hydrocarbon stream into a $C_{10}$ to $C_{13}$ hydrocarbon stream and at least one other paraffin stream; and
passing the $C_{10}$ to $C_{13}$ hydrocarbon stream to the dehydrogenation zone.

\* \* \* \* \*